United States Patent [19]

Voorhees

[11] 4,146,621

[45] Mar. 27, 1979

[54] PROCESS OF TREATING PROLIFERATIVE SKIN DISEASES

[75] Inventor: John J. Voorhees, Ann Arbor, Mich.

[73] Assignee: The Regents of the University of Michigan, Ann Arbor, Mich.

[21] Appl. No.: 808,446

[22] Filed: Jun. 21, 1977

Related U.S. Application Data

[60] Division of Ser. No. 646,633, Jul. 5, 1976, Pat. No. 4,034,087, which is a continuation-in-part of Ser. No. 425,065, Dec. 17, 1973, abandoned, which is a continuation-in-part of Ser. No. 324,012, Jan. 16, 1973, abandoned.

[51] Int. Cl.$^2$ ............... A61K 31/56; A61K 31/44; A61K 31/445

[52] U.S. Cl. .................. 424/240; 424/250; 424/263; 424/267

[58] Field of Search ............. 424/263, 240, 250, 267

[56] References Cited

PUBLICATIONS

Chem. Abst., 9th Collective Index, vol. 76-85 (1972-1976) p. 13096GS.

Primary Examiner—Sam Rosen
Attorney, Agent, or Firm—Neal A. Waldrop

[57] ABSTRACT

A process for alleviating proliferative skin diseases such as psoriasis, atopic dermatitis, etc., comprising administering to humans, or domesticated animals, topically and/or systemically a composition comprising a pharmaceutical carrier and at least one active compound selected from Groups 3, 4, 5, 6, 7 and 8 set forth in the specification, and combinations thereof with a glucocorticoid.

2 Claims, No Drawings

PROCESS OF TREATING PROLIFERATIVE SKIN DISEASES

CROSS-REFFERENCE TO RELATED APPLICATIONS

This application is filed pursuant to 35 USC 121; this application is a division of prior co-pending application Ser. No. 646,633, issued on July 5, 1977 as U.S. Pat. No. 4,034,087, for "Pharmaceutical Composition and Process of Treatment". Application Ser. No. 646,633 is a continuation-in-part of prior co-pending application Ser. No. 425,065, filed Dec. 17, 1973, now abandoned, which is a continuation-in-part application of prior co-pending application Ser. No. 324,012, filed Jan. 16, 1973, now abandoned.

BRIEF DESCRIPTION OF THE INVENTION

This invention relates to pharmaceutical compositions for and a method of treating psoriasis and related skin diseases characterized by epidermal cell proliferation. The compositions may be applied topically or by injection such that the composition enters the blood stream, or intralesionally, or intradermally, or subcutaneously or orally. The treatment may be either therapeutic or prophylactic.

DETAILED DESCRIPTION OF THE INVENTION

Humans and domesticated animals are afflicted with a wide variety of skin disorders or diseases. This invention relates to the treatment of that portion of skin diseases which is characterized by epidermal cell proliferation, or division, and may also be associated with incomplete tissue differentiation. Such diseases do not include carcinomas of the skin nor changes in skin cells during aging, or during the normal skin replacement cycle. Psoriasis is the most serious of the skin diseases with which this invention is concerned. These skin diseases are designated, in this specification and in the claims as "proliferative skin diseases" and other examples include atopic dermatitis, non-specific dermatitis, primary irritant contact dermatitis, allergic contact dermatitis, lamellar ichthyosis, epidermolytic hyperkeratosis, premalignant sun-induced keratosis, non-malignant keratosis and seborrheic dermatitis in humans, and atopic dermatitis and mange in domesticated animals.

Heretofore, proliferative skin diseases have been generally accepted by mankind as an ongoing evil having degrees of severity variable with time, with inherited skin traits and external factor: but always have been recognized as unsightly, painful, morbid diseases. Over the history of mankind innumerable medicines and treatments have been proposed, tried and used with varying degrees of success. However, no treatment heretofore devised or pharmaceutical composition used has been entirely successful.

The present day treatments of a commercial nature which are prescribed and used for the treatment of proliferative skin diseases include three approaches: (1) topical applications: coal tar derivatives, 5 fluorouracil, vitamin A acid, glucocorticoids in high dosage (constituting a non-permissive concentration), bath oils and non-specific emollient creams and ointments; (2) the systemic administration: glucocorticoids and classic anti-cancer agents, for example, methothrexate, hydroxyurea, azaribine, cyclophosphamide; (3) physical modalities; ultra violet light, x-irradiation, and in severe cases, surgery.

While these treatments provide, in certain cases, some remission of the original symptoms, each treatment suffers some defect, for example, temporary and/or incomplete mitigation of symptoms, rapid re-occurrence of the disease when treatment is terminated, serious and sometimes irreversible damage (atrophy) resulting from the topical application for extended times of glucocorticoids, acute bone marrow suppression and cirrhosis of the liver resulting from the protracted use of methothrexate which may lead to death of the patient, and the causation of cancer by the application of anti-cancer drugs, x-irradiation, or ultra violet rays.

Psoriasis is well-known to afflict two to three percent of the earth's population and is considered by most to be one of man's most unsightly, painful, morbid diseases. Psoriasis is a complex disorder of many varieties and is not completely medically understood even though extensive research and effort has been expended in the attempt to determine and identify its cause and to provide a cure. It is known that the epidermis of a psoriasis patient is characterized by excessive cell proliferation, incomplete terminal differentiation and glycogen accumulation. Although many compositions and methods for alleviating psoriasis have been proposed and used, only certain of them have been successful; even those considered successful usually alleviated the disease only for temporary periods. There is still a need for improved compositions and methods for treating psoriasis.

Previously existent compositions and treatments for psoriasis have provided in certain cases some remission of the original symptoms, or a temporary cure, but each composition or treatment heretofore known suffers from some defect to some degree. For a treatment to constitute a cure for psoriasis, it must be both safe and effective to cause an enduring remission of all the psoriasis lesions on the body to a degree such that they disappear and the skin assumes a normal appearance and is healthy and functional on a continuing basis. Alleviation of psoriasis to a degree less than a complete cure is useful and desirable because a treatment which accomplishes an alleviation in a seriously afflicted patient may be satisfactory to effect a substantially complete or permanent cure in a less seriously afflicted patient.

The primary object of this invention is to provide a pharmaceutical composition suitable for and a method of treating proliferating skin diseases. One of the more specific primary objectives of this invention is to provide a pharmaceutical composition for administration to psoriasis patients which is both capable of alleviating psoriasis and safe in application, even over an extended time period. Another object of this invention is to provide a method for treatment of psoriasis which is capable of effecting alleviation of the psoriasis in a short time period. A further object is to provide a cure for psoriasis, i.e., one which prevents a re-occurrence of the disease when the treatment is terminated.

In accordance with this invention it has been found that proliferative skin diseases are alleviated, that is, the symptoms of the disease are noticeably improved or become undetectable, by the treatment of the afflicted patient, or animal, with one or more of the pharmaceutical compositions described in detail hereinbelow.

For the purposes of this specification and the claims, a proliferative skin disease is alleviated when there is a noticeable decrease in the thickness of a lesion to palpation, with or without residual redness, or residual slightly dilated blood vessels or residual hyper- or hypo-pigmentation. For purposes of this invention and as claimed herein, psoriasis is alleviated when a scale-free psoriasis lesion is noticeably decreased in thickness, or noticeably but incompletely cleared, or completely cleared; indications of such alleviation include restoration of cell proliferation rate, and/or terminal differentiation, and/or glycogen content to near normal levels.

The compositions of this invention may be applied topically or by injection such that the composition enters the blood stream, or intradermally, intra- or peri-lesionally, or sub-cutaneously.

The term "topical" as employed herein relates to the use of the active ingredient incorporated in a suitable pharmaceutical carrier, and applied at the site of the disease for exertion of local action. Accordingly, such topical compositions include those pharmaceutical forms in which the compound is applied externally by direct contact with the skin surface to be treated. Conventional pharmaceutical forms for this purpose include ointments, lotions, pastes, jellies, sprays, aerosols, bath oils and the like. The term "ointment" embraces formulations (including creams) having oleaginous, absorption, water-soluble and emulsion-type bases, e.g., petrolatum, lanolin, polyethylene glycols, as well as mixtures thereof. It has been found that topical application with occlusion of an area larger than the medicated area produces improved results relative to non-occluded topical application and is, therefore, the preferred method of topical treatment with the compositions of this invention.

Certain of the compositions of this invention advantageously include skin penetrating adjuvants such as, for example, dimethyl sulfoxide, dimethyl acetamide, etc.

Injection "intradermally" refers to positioning the composition in the high dermis by needle injection, or by high pressure air injection.

Injection "intra- or peri-lesionally" refers to positioning the composition into the lesion or into the tissue adjacent to the lesion.

The compositions may be injected so as to reach the blood stream intramuscularly, subcutaneously, rectally by suppositories, sublingually, intravenously, orally, by inhalation, or by application to non-diseased skin.

The best mode of practicing the process of this invention is to treat the afflicted animal, or human, so as to cause a continuing release of the active compound at the afflicted site or sites, at a selected, controlled rate which is sustained for an extended time period. For example, epinephrine will be continuously released and provides sustained epinephrine activity for 9–10 hours by employing an aqueous suspension of crystalline epinephrine 1:200, in a sterile solution containing 0.5% phenol, 0.5% sodium thioglycollate, 1% sodium ascorbate, and 25% glycerine in water. This suspension may be administered subcutaneously in a dosage of 0.1–0.3 cc. of the suspension. Epinephrine activity is obtained substantially immediately from the epinephrine in suspension. Various modifications of the suspension ingredients, compatible with the particular active compound selected for injection may be made to obtain the desirable continuing and sustained active compound activity at the site being treated. Moreover, appropriate substitutions for the above mentioned suspension ingredients may be made to accommodate the selected active compound for topical or systemic administration to the afflicted patient, and similar enhanced results are obtained from such applications when the active compound is released over an extended time period.

The compositions of this invention comprise a pharmaceutical carrier and about 0.1% to about 15%, weight/volume, of at least one of the compounds selected from the groups:

1. Xanthines of the formula

wherein R and $R_1$ are selected from the group consisting of H, alkyl and hydroxyalkyl containing 1–7 carbon atoms, cycloalkyl containing 3–7 carbon atoms and aralkyl wherein the alkyl portion contains 1–7 carbon atoms, $R_2$ is H, alkyl (1–4), or a complex with ethylenediamine, and Y is selected from the group consisting of H or thiol;

2. Thioxanthines of the formula

wherein $R_1$ is selected from the group consisting of methyl, ethyl, propyl or —$CH_2$—$CH=CH_2$; $R_2$ is methyl, ethyl, propyl, —$CH_2CH=CH_2$, isopropyl, isobutyl, $CH_2CCH_3=CH_2$, pentyl, 3-methoxy-propyl, 2-methylbutyl, hexyl, benzyl, phenyl, phenethyl, or furfuryl; $R_3$ is selected from the group consisting of hydrogen, methyl or ethyl;

3. A compound of the formula

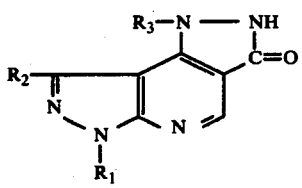

or

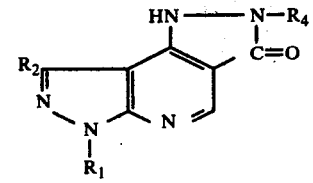

wherein $R_1$ is selected from the group consisting of lower alkyl of 1 to 7 carbon atoms, cycloalkyl of 3 to 6 carbon atoms, phenyl or $(R_4)_n$-phenyl, $(R_4)_n$—phenyl-lower alkyl wherein $R_4$ is hydrogen, lower alkyl as defined above, halogen, and hydroxy-lower alkyl wherein the carbon chain is 1–3, n is 1 or 2, $R_2$ is selected from the group consisting of hydrogen or lower alkyl, as defined above, $R_3$ is selected from the group consisting of hydrogen or lower alkyl as defined above and the physiologically acceptable acid addition salts thereof; R₄ is phenyl or simply substituted phenyl.

4. A compound of the formula

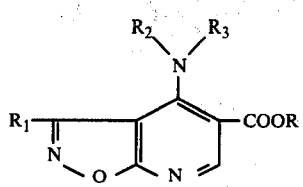

wherein R and R₁ are selected from the group consisting of hydrogen or lower alkyl of 1 to 3 carbon atoms, R₂ and R₃ are selected from the group consisting of hydrogen, lower alkyl of 1 to 4 carbon atoms, phenyl, benzyl, phenethyl, dialkylaminoalkyl in which alkyl is of 1-3 carbon atoms or taken together R₂ and R₃ form a heterocyclic ring, such as pyrrolidine, piperazino, piperidino, methylaziridino, 2,3-dimethylaziridino, 4-hydroxyethylpiperazino, and the pharmacologically acceptable acid addition salts.

5. A compound of the formula

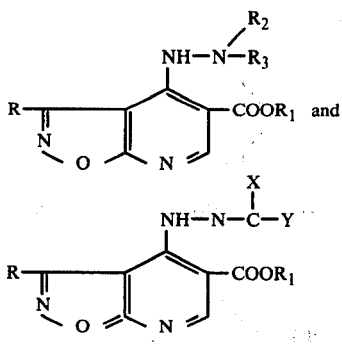

wherein R and R₁ each is hydrogen, lower alkyl of 1-8 carbon atoms, benzyl or phenylethyl, R₂ is hydrogen, lower alkyl of 1-8 carbon atoms or phenyl, R₃ is hydrogen, lower alkyl defined as above or lower alkanoyl in which the acyl radical is of 1-8 carbon atoms, providing that only one R is a phenyl containing substituent, and physiologically acceptable acid addition salts thereof, X represents hydrogen, lower alkyl, hydroxy-lower alkyl, phenyl, substituted phenyl, phenyl-lower alkyl or substituted phenyl-lower alkyl, Y represents lower alkyl, phenyl, hydroxy-lower alkyl, substituted phenyl, phenyl-lower alkyl or substituted phenyl-lower alkyl and together X and Y are cycloalkyl.

6. A compound of the formula

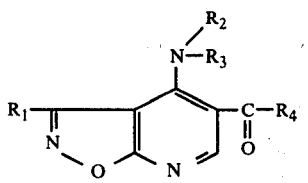

wherein R and R₁ are selected from the group consisting of hydrogen or lower alkyl of 1 to 3 carbon atoms, R₂ and R₃ are selected from the group consisting of hydrogen, lower alkyl of 1 to 4 carbon atoms, phenyl, benzyl, phenethyl, dialkylaminoalkyl in which alkyl is of 1-3 carbon atoms or taken together R₂ and R₃ form a heterocyclic ring, such as pyrrolidino, piperazino, piperidino, methylaziridino, 2,3-dimethylaziridino, 4-hydroxyethylpiperazino, and the pharmacologically acceptable acid addition salts, and R₄ is lower alkyl, cyclo-lower alkyl, phenyl, hydroxyphenyl or hydroxy-lower alkylphenyl.

7. A compound of the formula

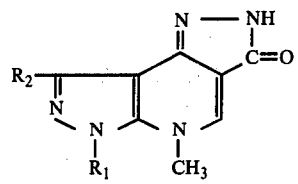

wherein R₁ is lower alkyl of 1-7 carbon atoms, phenyl, benzyl or phenethyl and R₂ is hydrogen or lower alkyl.

8. A compound of the formula

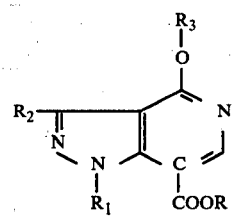

wherein R is hydrogen or alkyl of up to 12 carbon atoms, R₁ is hydrogen, lower alkyl as defined above, meta- or para- R₄,R₅-benzoyl, phenyl, benzyl or phenethyl, R₂ is hydrogen, lower alkyl defined as above, phenyl, benzyl or phenethyl, R₃ is lower alkyl as above, benzyl or phenethyl, R₄ and R₅ each is hydrogen, halogen, methyl or methoxy, and physiologically acceptable acid addition salts thereof;

9. A compound selected from the group consisting of compounds characterized by the formula

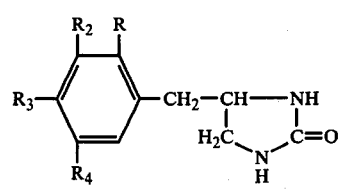

wherein R is halogen, hydrogen, lower alkyl and lower alkoxy; R₂, R₃ and R₄ taken independently of each other are hydrogen, lower alkoxy or hydroxy-lower alkoxy and provided that R₂, R₃ and R₄ taken independently of each other represent at least one oxygenated substituent; or R, R₂, R₃ and R₄ taken as an adjacent pair of methylenedioxy and the optical antipodes thereof;

10. A compound of the formula

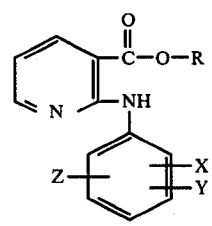

where R is hydrogen or —CH₂CHOHCH₂OH, X is lower alkyl of from 1 to 8 carbon atoms, lower alkoxy of from 1 to 8 carbon atoms, chloro, bromo —CH₃, $NO_2$, Y is chloro, bromo, $-CH_3$, $NO_2$, lower alkyl of from 1 to 8 carbon atoms, Z is hydrogen, halogen, $CF_3$, lower alkyl of from 1 to 8 carbon atoms inclusive;

11. A compound of the formula

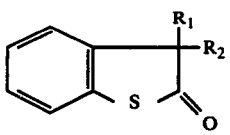

where $R_1$ is hydroxy,
$R_2$ is

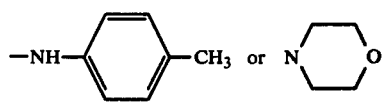

and $R_1$ and $R_2$ taken together can be

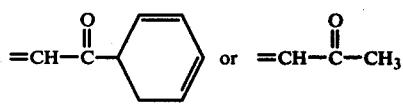

12. A compound of the formula

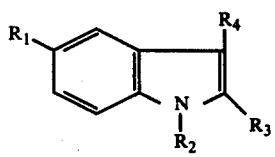

wherein $R_1$ is hydrogen or methoxy
$R_2$ is $-CH_3$

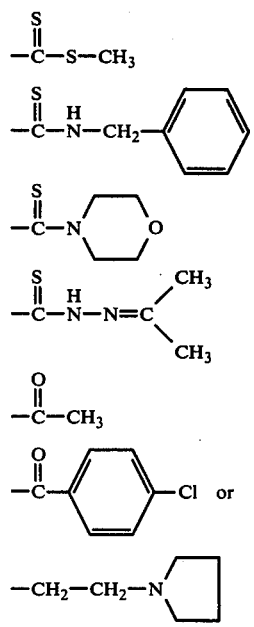

$R_3$ is hydrogen, methyl, phenyl or

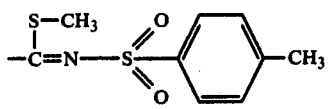

$R_4$ is hydrogen, hydroxy

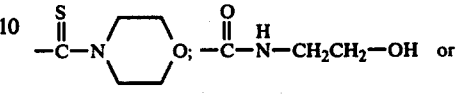 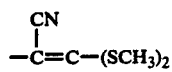

13. A compound of the formula

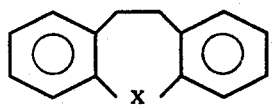

$X=N-R_1$; wherein $R_1$ is

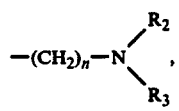

$n=1-3$, $R_2$ and $R_3$ are H or methyl or $X=C=R_4$ wherein $R_4$ is

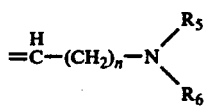

$n=1-3$ and $R_5$ and $R_6$ = H or methyl;

14. and at least one number selected from the group consisting of
  Pentylenetetrazole
  Methylphenidate
  Bunamidine
  Pyrvinium pamoate
  Meprobamate
  Phenacemide
  Dipyridamol
  Indomethacin
  Chlordiazopoxide
  Nicotinamide
  Diazepam
  Disodium chromoglycate
  Levamisole
  Diazoxide
  Aldosterone
  Nigroglycerine
  Amyl nitrate
  Sodium nitrate
  Isosorbide dinitrate
  Nicotinic acid
  Cyclandelate
  Erythritol tetra-nitrate
  Pentaerythritol tetra-nitrate
  Minoxidil and
  Quazodine
said compounds being in association with a pharmaceutical carrier wherein the concentration of said active component is effective to alleviate a proliferative skin disease.

The compositions of this invention may be employed in conjunction with glucocorticoids. The expression "glucocorticoids" refers to a naturally occurring product of the adrenal cortex, or a synthetic analog thereof possessing anti-inflammatory activity and minimal or no mineralocorticoid activity or sex steroid activity. Of the natural glucocorticoids, one may use for example, hydrocortisone or the synthetic glucocorticoids such as methyl prednisolone acetate (Prednisone) for oral application or triamcinolone for topical therapy. The glucocortcoids should be employed in minor amounts or "permissive dosage". The expression "permissive dosage" for glucocorticoids refers to a quantity which minimally supplements the natural output of adrenal cortical glucocorticoids in a normal person and which dosage administered, alone, has no perceptible effect on proliferative skin diseases.

The quantity of the active compound to be used in the compositions of this invention for administration topically, parenterally or systemically ranges from about 0.1% to about 15% weight/volume topically; from about 0.1% to about 10% w/v parenterally; and for oral dosage forms the % amount of active ingredient is determined by the physical characteristics of the carrier with regard to manufacturing requirements and elegance.

The compositions of the present invention are presented for systemic administration to humans and animals in unit dosage forms, such as tablets, capsules, pills, powders, granules, sterile parenteral solutions or suspensions, and oral solutions or suspensions, and oil-water emulsions containing suitable quantities of one or more of the active compounds above described.

For oral administration either solid or fluid unit dosage forms can be prepared. For preparing solid compositions such as tablets, the principal active ingredient is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. The tablets can be laminated or otherwise compounded to provide a dosage form affording the advantage of prolonged or delayed action or predetermined successive action of the enclosed medication. For example, the tablet can comprise an inner dosage and an outer dosage component, the latter being in the form of an envelope over the former.

Alternatively, the two component system can be utilized for preparing tablets containing two or more incompatible active ingredients. Wafers are prepared in the same manner as tablets, differing only in shape and the inclusion of sucrose or other sweetener and flavor. In their simplest embodiment, capsules, like tablets, are prepared by mixing the active compound or compounds with an inert pharmaceutical diluent and filling the mixture into a hard gelatin capsule or appropriate size. In another embodiment, capsules are prepared by filling hard gelatin capsules with polymeric acid coated beads containing the active compound or compounds. Soft gelatin capsules are prepared by machine encapsulation of a slurry of the active compound or compounds with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared of the insoluble forms with a syrup vehicle with the aid of a suspending agent such as acacia, tragacenth, methylcellulose and the like.

Topical ointments can be prepared by dispersing the active compound or compounds in a suitable ointment base such as petrolatum, lanolin, polyethylene glycol, mixtures thereof, and the like. Advantageously, the active compound of compounds is finely divided by means of a colloid mill utilizing light liquid petrolatum as a levigating agent prior to dispersing in the ointment base. Topical creams and lotions are prepared by dispersing the active compound or compounds in the oil phase prior to the emulsification of the oil phase in water.

For parenteral administration of the dosage forms are prepared utilizing the active compound or compounds and a sterile vehicle, water being preferred. The compound, depending on the form and concentration used, can be either suspended or dissolved in the vehicle. In preparing solutions, a water-soluble form of the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution.

For parenteral or systemic administration of the compositions of this invention, the usual dosage of the selected active compound, or compounds, should be employed.

The compositions of this invention may include one or more of the above identified active compounds in a single composition or the method of the invention may be practiced by the administration of a plurality of compositions, each of which contains a single or a plurality of active compounds. In certain cases, the method of the invention may involve the administration of compositions containing a single active compound or a mixture of active compounds by a plurality of the forms of the administration, for example by a combination of oral and/or injection and/or topical application, etc.

In other cases the method of this invention is advantageously practiced by combining the administration forms in a time spaced sequence, for example, by using systemic application of one or more of the compositions for a time period and then applying one or more compositions topically, or by injection while continuing the systemic application, etc.

The following examples identify certain compositions which typify the manner of combining selected active compounds with a pharmaceutical carrier for use in the process of treatment of proliferative skin diseases as above generally described, but they are not intended to represent the limits of either the compositions of or the process of this invention which is defined in the claims.

EXAMPLE 1

Capsules

One thousand two-piece hard gelatin capsules for oral use, each containing 200 mg. of 1-methyl-3-isobutyl-xanthine are prepared from the following types and amounts of materials:

| | |
|---|---|
| 1-Methyl-3-isobutyl-xanthine | 50 gm. |
| Corn starch | 250 gm. |
| Talc | 75 gm. |
| Magnesium stearate | 2.5 gm. |

The materials are thoroughly mixed and then encapsulated in the usual manner.

The foregoing capsules are useful for the systemic treatment of psoriasis in adult humans by the oral administration of 1 capsule every 6 hours.

Using the procedure above, capsules are similarly prepared containing in 25, 75, and 100 mg. amounts by substituting 25, 75, and 100 gm. of 1-methyl-3-isobutylxanthine for the 50 gm. used above.

EXAMPLE 2

Capsules

One thousand two-piece hard gelatin capsules for oral use, each containing 100 mg. of 1-methyl-3-isobutylxanthine are prepared from the following types and amounts of ingredients:

| | |
|---|---|
| 1-Methyl-3-isobutyl-xanthine | 100 gm. |
| Corn starch | 250 gm. |
| Talc | 75 gm. |
| Magnesium stearate | 2.5 gm. |

The ingredients are thoroughly mixed and then encapsulated in the usual manner.

The foregoing capsules are useful for the systemic treatment of psoriasis in adult humans by the oral administration of 1 capsule four times a day.

EXAMPLE 3

Tablets

One thousand tablets for oral use, each containing 50 mg. of 1-methyl-3-isobutyl-xanthine are prepared from the following types and amounts of materials:

| | |
|---|---|
| 1-Methyl-3-isobutyl-xanthine | 50 gm. |
| Lactose | 125 gm. |
| Corn starch | 65 gm. |
| Magnesium stearate | 7.5 gm. |
| Light liquid petrolatum | 3 gm. |

The ingredients are thoroughly mixed and slugged. The slugs are broken down by forcing through a number sixteen screen. The resulting granules are then compressed into tablets, each tablet containing 50 mg. of 1-methyl-3-isobutyl-xanthine.

The foregoing tablets are useful for systemic treatment of psoriasis in adult humans by oral administration of 1 tablet every 6 hours.

EXAMPLE 4

Oral syrup

One thousand cc. of an aqueous suspension for oral use, containing in each 5 cc. dose 100 mg. of 1-methyl-3-isobutyl-xanthine is prepared from the following types and amounts of ingredients:

| | |
|---|---|
| 1-Methyl-3-isobutyl-xanthine | 40 gm. |
| Citric acid | 2 gm. |
| Benzoic acid | 1 gm. |
| Sucrose | 700 gm. |
| Tragacanth | 5 gm. |
| Lemon oil | 2 cc. |
| Deionized water q.s. | 1000 cc. |

The citric acid, benzoic acid, sucrose, tragacanth, and lemon oil are dispersed in sufficient water to make 850 cc. of solution the 1-methyl-3-isobutyl-xanthine is stirred into the syrup until uniformly distributed. Sufficient water is added to make 1000 cc.

The composition so prepared is useful in the systemic treatment of psoriasis in adult humans at a dose of 1 teaspoonful 4 times a day.

EXAMPLE 5

Parenteral solution

A sterile aqueous solution for intramuscular use, containing in 1 cc. 50 mg. of 1-methyl-3-isobutyl-xanthine is prepared from the following types and amounts of materials:

| | |
|---|---|
| 1-Methyl-3-isobutyl-xanthine | 50 gm. |
| Lidocaine hydrochloride | 4 gm. |
| Methylparaben | 2.5 gm. |
| Propylparaben | 0.17 gm. |
| Water for injection q.s. | 1000 cc. |

The ingredients are dissolved in the water and the solution sterilized by filtration. The sterile solution is filled into vials and the vials sealed.

The composition is useful in the systemic treatment of psoriasis at a dose of 1 cc. I.M. 4 times a day.

EXAMPLE 6

Parenteral solution

A sterile aqueous solution for intradermal use, containing in 1 cc. 15 mg. of 1-methyl-3-isobutyl-xanthine is prepared from the following types and amounts of ingredients:

| | |
|---|---|
| 1-Methyl-3-isobutyl-xanthine | 15 gm. |
| Sodium chloride 10% Solution q.s. | |
| Water for injection q.s. | 1000 cc. |

The 1-methyl-3-isobutyl-xanthine is added to the water and sufficient sodium chloride added to form an isotonic solution and the solution sterilized by filtration.

The sterile solution is administered intradermally by high pressure injection for treatment os psoriasis.

EXAMPLE 7

Topical ointment

One thousand gm. of 10% ointment is prepared from the following types and amounts of ingredients:

| | |
|---|---|
| 1-Methyl-3-isobutyl-xanthine | 100 gm. |
| Liquid petrolatum (heavy) | 250 gm. |
| Wool fat | 200 gm. |
| White petrolatum q.s. | 1000 gm. |

The white petrolatum and wool fat are melted and 100 gm. of liquid petrolatum added thereto. The 1-methyl-3-isobutyl-xanthine added to the remaining liquid petrolatum and the mixture milled until the powder is finely divided and uniformly dispersed. The powder mixture is stirred into the white petrolatum mixture and stirring continued until the ointment congeals.

The foregoing ointment is usefully applied topically to the skin of animals for the treatment of mange.

EXAMPLE 8

Cream

One thousand grams of a topical cream are prepared from the following types and amounts of ingredients:

| | |
|---|---|
| 1-Methyl-3-isobutyl-xanthine | 50 gm. |
| Tegacid Regular* | 150 gm. |
| Spermaceti | 100 gm. |
| Propylene glycol | 50 gm. |
| Polysorbate 80 | 5 gm. |
| Methylparaben | 1 gm. |
| Deionized water q.s. | 1000 gm. |

*Self-emulsifying glyceryl monostearate from Goldschmidt Chemical Corporation, New York, N.Y.

The Tegacid and spermaceti are melted together at a temperature of 70°–80° C. The methylparaben is dissolved in about 500 gm. of water and the propylene glycol, polysorbate 80, and 1-methyl-3-isobutyl-xanthine are added in turn, maintaining a temperature of 75°–80° C. The methylparaben mixture is added slowly to the Tegacid and spermaceti melt, with constant stirring. The addition is continued for at least 30 minutes with continued stirring until the temperature has dropped to 40°–45° C. The pH of the final cream is adjusted to 3.5 by adding 2.5 gm. of citric acid and 0.2 gm. of dibasic sodium phosphate dissolved in about 50 gm. of water. Finally, sufficient water is added to bring the final weight to 1000 gm. and the preparation stirred to maintain homogeneity until cooled and congealed.

The foregoing composition is useful for the treatment of psoriasis by applying to the lesions with occulsive bandage.

EXAMPLE 9

| | |
|---|---|
| 1-Methyl-3-isobutyl-xanthine | 1000 gm. |
| Cetyl alcohol | 600 gm. |
| Stearyl alcohol | 600 gm. |
| Aerosol OT | 150 gm. |
| White petrolatum | 3000 gm. |
| Propylene glycol | 1000 ml. |
| Distilled water q.s. | 10,000 gm. |

The 1-methyl-3-isobutyl-xanthine is mixed with the white petrolatum and stirred with a melt of the alcohols and propylene glycol. The aerosol OT is dissolved in 5000 cc. of water and an emulsion formed with the petrolatum mix, sufficient water being added to make 10,000 grams.

The cream is applied to psoriatic lesions twice daily with occlusive bandage.

Optionally, following the procedure of the preceding example, substituting 2,000 grams of dimethylacetamide for 2000 grams of water a composition is obtained providing better penetration of the active ingredient into the skin.

EXAMPLE 10

Capsules

One thousand two-piece hard gelatin capsules for oral use, each containing 25 gm. of 4(3-butoxy-3-methoxybenzyl)-2-imidazolidinone are prepared from the following types and amounts of materials:

| | |
|---|---|
| 4(3-butoxy-3-methoxybenzyl)-2-imidazolidinone | 25 gm. |
| Corn starch | 250 gm. |
| Talc | 75 gm. |
| Magnesium stearate | 2.5 gm. |

The materials are thoroughly mixed and then encapsulated in the usual manner.

The foregoing capsules are useful for the systemic treatment of psoriasis in adult humans by the oral administration of 1 capsule every 4 hours.

Using the procedure above, capsules are similarly prepared containing in 5, 10, and 100 mg. amounts by substituting 5, 10, and 100 gm. of 4(3-butoxy-3-methoxybenzyl)-2-imidazolidinone for the 25 gm. used above.

EXAMPLE 11

Capsules

One thousand two-piece hard gelatin capsules for oral use, each containing 25 mg. of 4(3-butoxy-3-methoxybenzyl)-2-imidazolidinone are prepared from the following types and amounts of ingredients:

| | |
|---|---|
| 4(3-butoxy-3-methoxybenzyl)-2-imidazolidinone | 25 gm. |
| Corn starch | 250 gm. |
| Talc | 75 gm. |
| Magnesium stearate | 2.5 gm. |

The ingredients are thoroughly mixed and then encapsulated in the usual manner.

The foregoing capsules are useful for the systemic treatment of psoriasis in adult humans by the oral administration of 1 capsule twice a day.

EXAMPLE 12

Tablets

One thousand tablets for oral use, each containing 10 mg. of 4(3-butoxy-3-methoxybenzyl)-2-imidazolidinone are prepared from the following types and amounts of materials:

| | |
|---|---|
| 4(3-butoxy-3-methoxybenzyl)-2-imidazolidinone | 50 gm. |
| Lactose | 125 gm. |
| Corn starch | 65 gm. |
| Magnesium stearate | 7.5 gm. |
| Light liquid petrolatum | 3 gm. |

The ingredients are thoroughly mixed and slugged. The slugs are broken down by forcing through a number sixteen screen. The resulting granules are then compressed into tablets, each tablet containing 10 mg. of 4(3-butoxy-3-methoxybenzyl)-2-imidazolidinone.

The foregoing tablets are useful for systemic treatment of psoriasis in adult humans by oral administration of 1 tablet every 4 hours.

EXAMPLE 13

Oral syrup

One thousand cc. of an aqueous suspension for oral use, containing in each 5 cc. dose 25 mg. of 4(3-butoxy-3-methoxybenzyl)-2-imidazolidinone is prepared from the following types and amounts of ingredients:

| | |
|---|---|
| 4(3-butoxy-3-methoxybenzyl)-2-imidazolidinone | 5 gm. |
| Citric acid | 2 gm. |
| Benzoic acid | 1 gm. |
| Sucrose | 700 gm. |
| Tragacanth | 5 gm. |
| Lemon oil | 2 cc. |
| Deionized water q.s. | 1000 cc. |

The citric acid, benzoic acid, sucrose, tragacanth, and lemon oil are dispersed in sufficient water to make 850 cc. of solution. The 4(3-butoxy-3-methoxybenzyl)-2-imidazolidinone is stirred into the syrup until uniformly distributed. Sufficient water is added to make 1000 cc.

The composition so prepared is useful in the systemic treatment of psoriasis in adult humans at a dose of 1 teaspoonful 4 times a day.

EXAMPLE 14

Parenteral solution

A sterile aqueous solution for intramuscular use, containing in 1 cc. 5 mg. of 4(3-butoxy-3-methoxybenzyl)-2-imidazolidinone is prepared from the following types and amounts of materials:

| | |
|---|---|
| 4(3-butoxy-3-methoxybenzyl)-2-imidazolidinone | 5 gm. |
| Lidocaine hydrochloride | 4 gm. |
| Methylparaben | 2.5 gm. |
| Propylparaben | 0.17 gm. |
| Water for injection q.s. | 1000 cc. |

The ingredients are dissolved in the water and the solution sterilized by filtration. The sterile solution is filled into vials and the vials sealed.

The composition is useful in the systemic treatment of psoriasis at a dose of 1 cc. I.M. 4 times a day.

EXAMPLE 15

Parenteral solution

A sterile aqueous solution for intradermal use, containing in 1 cc. 5 mg. of 4(3-butoxy-3-methoxybenzyl)-2-imidazolidinone is prepared from the following types and amounts of ingredients:

| | |
|---|---|
| 4(3-butoxy-3-methoxybenzyl)-2-imidazolidinone | 5 gm. |
| Sodium chloride 10% Solution q.s. | |
| Water for injection q.s. | 1000 cc. |

The 4(3-butoxy-3-methoxybenzyl)-2-imidazolidinone is added to the water and sufficient sodium chloride added to form an isotonic solution and the solution sterilized by filtration.

The sterile solution is administered intradermally by high pressure injection for treatment of psoriasis.

EXAMPLE 16

Topical ointment

One thousand gm. of 10% ointment is prepared from the following types and amounts of ingredients:

| | |
|---|---|
| 4(3-butoxy-3-methoxybenzyl)-2-imidazolidinone | 100 gm. |
| Liquid petrolatum (heavy) | 250 gm. |
| Wool fat | 150 gm. |
| White petrolatum q.s. | 1000 gm. |

The white petrolatum and wool fat are melted and 100 gm. of liquid petrolatum added thereto. The 4(3-butoxy-3-methoxybenzyl)-2-imidazolidinone is added to the remaining liquid petrolatum and the mixture milled until the powder is finely divided and uniformly dispersed. The powder mixture is stirred into the white petrolatum mixture and stirring continued until the ointment congeals.

The foregoing ointment is usefully applied topically to the skin of animals for the treatment of mange.

EXAMPLE 17

Cream

One thousand grams of a topical cream are prepared from the following types and amounts of ingredients:

| | |
|---|---|
| 4(3-butoxy-3-methoxybenzyl)-2-imidazolidinone | 50 gm. |
| Tegacid Regular* | 150 gm. |
| Spermaceti | 100 gm. |
| Propylene glycol | 50 gm. |
| Polysorbate 80 | 5 gm. |
| Methylparaben | 1 gm. |
| Deionized water q.s. | 1000 gm. |

*Self-emulsifying glyceryl monostearate from Goldschmidt Chemical Corporation, New York, N.Y.

The Tegacid and spermaceti are melted together at a temperature of 70°–80° C. The methylparaben is dissolved in about 500 gm. of water and the propylene glycol, polysorbate 80, and 4(3-butoxy-3-methoxybenzyl)-2-imidazolidinone are added in turn, maintaining a temperature of 75°–80° C. The methylparaben mixture is added slowly to the Tegacid and spermaceti melt, with constant stirring. The addition is continued for at least 30 minutes with continued stirring until the temperature has dropped to 40°–45° C. The pH of the final cream is adjusted to 3.5 by adding 2.5 gm. of citric acid and 0.2 gm. of dibasic sodium phosphate dissolved in about 50 gm. of water. Finally, sufficient water is added to bring the final weight to 1000 gm. and the preparation is stirred to maintain homogeneity until cooled and congealed.

The foregoing composition is useful for the treatment of psoriasis by applying to the lesions with occlusive bandage.

EXAMPLE 18

| | |
|---|---|
| 4(3-butoxy-3-methoxybenzyl)-2-imidazolidinone | 1000 gm. |
| Cetyl alcohol | 600 gm. |
| Stearyl alcohol | 600 gm. |
| Aerosol OT | 150 gm. |
| White petrolatum | 3000 gm. |
| Propylene glycol | 1000 ml. |
| Distilled water q.s. | 10,000 gm. |

The 4(3-butoxy-3-methoxybenzyl)-2-imidazolidinone is mixed with the white petrolatum and stirred with a melt of the alcohols and propylene glycol. The aerosol OT is dissolved in 5000 cc. of water and an emulsion formed with the petrolatum mix, sufficient water being added to make 10,000 grams.

The cream is applied to psoriatic lesions twice daily with occlusive bandage.

Optionally, following the procedure of the preceding example, substituting 2,000 grams of dimethylacetamide for 2,000 grams of water a composition is obtained providing better penetration of the active ingredient into the skin.

EXAMPLE 19

Following the procedure of the preceding Examples 1 to 18, inclusive, substituting a therapeutic dosage amount each of 1-methyl-3-isobutyl-xanthine, 6-thio theophylline, 1,6-dimethyl-1,6-dihydro-dipyrazolo(3,4-b:3',4'-d)pyridin-3-one, 4-dimethylamino-5-methoxycarbonyl-3-methylisoxayolo(5,4-b)pyridine, 5-ethoxycarbonyl-4-(2-tertiarybutylhydrazino)-3-methylisoxayolo-(5,4-b(pyridine, 5-acetyl-4-piperazino-3-methylisoxayolo-(5,4-b)pyridine, 5,6,8-trimethyl-dipyriazolo(3,4-b:3',4'-d)pyridin-3(2H)-one, 4-ethoxy-1-ethyl-3-methyl-1H-pyrazolo(4,3-c)pyridine-7-carboxylic acid ethyl ester, 4-[3-(n-butoxy)-4-methoxybenzyl]2-imidazolidinone, glyceryl-2-(2,6-dimethylanilino)nicotinate, 1-oxo-2-acetonylidenebenzo(b)thiophen, N-[1-(pyrrolidino)ethyl]-2-phenyl-5-methoxyindole, imipramine for the 4(3-butoxy-3-methoxybenzyl)-2-imidazolidinone, compositions are prepared which are useful for the treatment of psoriasis.

EXAMPLE 20

The compositions prepared in the preceding examples 1 through 19, inclusive, can similarly be administered for treatment of atopic dermatitis, non-specific dermatitis, basal and squamous cell carcinomas of the skin, lamellar ichthyosis, epidermolytic hyperkeratosis, premalignant sun induced keratosis, non-malignant keratosis, acne, and seborrheic dermatitis in humans and atopic dermatitis and mange in domesticated animals.

EXAMPLE 21

Advantageously, following the therapy of Examples 1 to 19, inclusive, additional benefits can be obtained with concurrent or sequential oral administration of 20 mg. of prednisone twice a week.

EXAMPLE 22

Seventeen psoriasis patients were selected and used in the clinical study consisting of the application four times per day on two selected lesion on each patient of a cream, and the same cream containing 1% RO 20-1724*, w/v, over a four-week period. Neither the doctor nor the patient was aware of which of the cream samples contained the active ingredient RO 20-1724. The cream was applied in a light layer to the entire surface of the lesion, with or without slight rubbing to make the overlying film uniform and then the coated lesion was covered with a bandage, i.e., a plastic bandage having minimal porosity for air passage such that the lesion was substantially isolated from air at all times, except during application. 6 *d,1-4-(3-butoxy-4-methoxybenzyl)-2-imidazolidinone.

Examination of the psoriatic lesions was made by three doctors, each of whom made independent appraisals of the appearance of the lesion at its center and at the edge and assigned a rating to the condition thereof using 0 or 1 to mean no change in the appearance, a 2 or 3 meaning an improvement, that is, an alleviation of the psoriatic lesion as to redness or degree of scaling, or both; when the evaluation of a patient by 2 of the doctors was not the same, the lower score was used for statistical analysis.

The selection of lesion location on each patient was one lesion on the left side of the body and the other lesion on the right side of the body and the evaluations of appearance of the lesions are recorded in Table I, left or right; the right-hand column of Table I contains the code for the portion of the body of each patient, i.e., left or right, which received the cream containing the RO 20-1724 compound, and the results can be correlated directly for the two-week evaluation and the four-week evaluation.

TABLE I

| PATIENT | 2nd Week Evaluation | | | | 4th Week Evaluation | | | | RO 20-1724 SITE |
|---|---|---|---|---|---|---|---|---|---|
| | Right | | Left | | Right | | Left | | |
| | C | E | C | E | C | E | C | E | |
| 1 | 2 | 1 | 3 | 2 | 0 | 0 | 3 | 0 | LEFT |
| 2 | 3 | 2 | 0 | 0 | 3 | 3 | 0 | 0 | RIGHT |
| 3 | 3 | 2 | 1 | 1 | 3 | 3 | 0 | 0 | RIGHT |
| 4 | 2 | 2 | 2 | 2 | 1 | 1 | 3 | 2 | LEFT |
| 5 | 0 | 0 | 1 | 1 | 0 | 0 | 0 | 0 | LEFT |
| 6 | 1 | 1 | 1 | 1 | 3 | 2 | 1 | 1 | RIGHT |
| 7 | 3 | 3 | 2 | 2 | 3 | 3 | 1 | 1 | RIGHT |
| 8 | 1 | 0 | 2 | 1 | 0 | 0 | 2 | 1 | LEFT |
| 9 | 2 | 1 | 0 | 0 | — | — | — | — | RIGHT |
| 10 | 1 | 1 | 1 | 1 | 3 | 2 | 1 | 1 | RIGHT |
| 11 | 1 | 1 | 0 | 0 | 2 | 1 | 1 | 1 | LEFT |
| 12 | — | — | — | — | — | — | — | — | LEFT |
| 13 | 0 | 0 | 0 | 0 | 0 | 0 | 0 | 0 | RIGHT |
| 14 | 0 | 0 | 0 | 0 | 0 | 2 | 0 | 0 | RIGHT |
| 15 | 0 | 0 | 2 | 1 | 0 | 0 | 2 | 2 | LEFT |
| 16 | 2 | 1 | 0 | 0 | 3 | 1 | 0 | 0 | LEFT |
| 17 | 1 | 1 | 2 | 2 | — | — | — | — | LEFT |

C Center of lesion
E Edge of lesion
O the circled ratings are those related to the RO 20 site
Improved rating - 2 or 3
Unimproved rating - 0 or 1

Of the original 17 patients who entered the study, 14 were included in the second week evaluation analysis, and 12 in the analysis of the fourth week evaluations.

No. 14 and No. 16 were not included at all, on the basis of their non-conformance to the protocol, e.g., not occluding, not returning for evaluation until 3 weeks instead of 2 and not applying the cream regularly.

No. 12 requested to be removed from the study at the time of this first evaluation; the lesions couldn't be evaluated at that time because he had not been using the occlusion.

No. 9 and No. 17 also requested to be removed soon after the first evaluation because their untreated psoriasis was flaring. They are included in the 2nd week analysis, because they both applied the cream and occluded the lesions for the two weeks they were involved.

Based upon the results set forth in the above Table I, it is apparent that there were statistically significantly more improved lesions treated with RO 20-1724 for both the center and edge of the 4th week. The center was also significantly improved with RO 20-1724 at the second week. This double blind clinical evidence on psoriatic humans proves that d,1-4-(3-butyxy-4-methoxybenzyl)-2-imidazolidinone functions to alleviate proliferative skin diseases, specifically psoriasis. Since psoriasis is the most difficult of the proliferative skin disease to alleviate, this test demonstrates that the tested compound has utility in alleviating proliferative skin diseases as that term is defined above.

An improved form of this invention has now been found whereby psoriasis may be alleviated in a shorter time and to a greater than expected degree than obtainable by the processes described hereinabove. This improved invention comprises the concurrent administration to an afflicted human or animal of a composition comprising active compounds in association with a pharmaceutical carrier wherein said compounds are present in an amount in the range of about 0.1% to about 10% w/v, the composition containing at least one active compound selected from each of two groups.

The first group of active compounds consists of isoproterenol, salbutamol, epinephrine, nor-epinephrine, ephedrine, and prostaglandin $E_1$ and $E_2$. Prostaglandin E-type compounds and their esters are known in the art. See, for example, Bergstrom S., et al. P'Col Reviews 20:1 (1968) for $PGE_1$, $PGE_2$.

The second group of active compounds consists of 1-methyl-3-isobutyl xanthine, caffeine, theophylline, diazepam, papaverine, 1-ethyl-4-(isopropylidenehydrazino)-1H-pyrazolo(3,4-b)-pyridine-5-carboxylic acid, ethyl ester, HCl, and a compound having the formula:

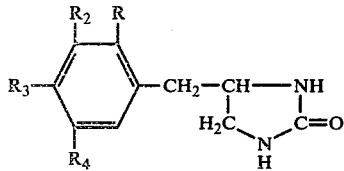

wherein R is halogen, hydrogen, lower alkyl and lower alkoxy; $R_2$, $R_3$ and $R_4$ taken independently of each other are hydrogen, lower alkoxy or hydroxy-lower alkoxy and provided that $R_2$, $R_3$ and $R_4$ taken independently of each other represent at least one oxygenated substituent; or R, $R_2$, $R_3$ and $R_4$ taken as an adjacent pair is methylenedioxy and the optical antipodes thereof.

The combination of material from Group I and Group II is even further enhanced in its ability to alleviate psoriasis, as to time or concentration of the material from Group I or Group II which is required to be effective, by the inclusion in the combination of a glucocorticoid. The expression "glucocorticoid" refers to a naturally occurring product of the adrenal cortex, or a synthetic analog thereof possessing anti-inflammatory activity and minimal or no mineralocorticoid activity or sex steroid activity. Of the natural glucocorticoids, one may use for example, hydrocortisone or the synthetic glucocorticoids such as methyl prednisolone acetate (Prednisone) for oral application or triamcinolone for topical therapy.

The quantity of the compounds from Groups I or II to be used in the compositions of this invention for administration topically, parenterally or systemically ranges from about 0.1% to about 10% w/v topically; from about 0.1% to about 10% w/v parenterally or orally. The amount of each of the materials from Groups I and II or any particular composition may be varied over a wide range depending upon the severity of the psoriasis, the patient's reaction to drugs, as above generally described in connection with the over-all objective of safety of administration; the quantity of each of the materials from Group I and Group II also varies as a function of degree of synergism which results from a particular combination of materials that is selected with the over-all objective being the selection of the minimal quantity of each material of the combination which will provide alleviation of the psoriasis in the particular patient. For example, the degree of synergism exhibited by the combination of isoproterenol and theophylline exceeds the synergism resulting from the combination of isoproterenol and caffeine.

Thus, the quantity of isoproperenol and theophylline may satisfactorily range from one-hundredth of the amount of isoproterenol which is required to activate the epidermal adenolate cyclase to a degree sufficient to alleviate psoriasis up to an amount of about one-third the quantity of isoproterenol which is effective for that purpose, and the quantity of theophylline may satisfactorily vary from about one-hundredth of the amount of theophylline which is required to inhibit epidermal phosphodiasterase to a degree sufficient to alleviate psoriasis when applied separately, up to an amount of about one-third the quantity of theophylline sufficient to effectively alleviate psoriasis. In contrast, the range for isoproterenol in combination with caffeine may satisfactorily vary from about one-fifth up to about one-third satisfactorily vary from about one-fifth up to about one-third of the amount of isoproterenol which is required to alleviate psoriasis when applied alone, in combination with about one-fifth up to about one-third of the amount of caffeine required to effectively inhibit epidermal phosphodiesterase when applied alone, in order to achieve the synergistic cooperation to alleviate psoriasis when administered in combination. In general, the minimum quantity of the selected material from Group I may satisfactorily form about 1/100th to about ⅓rd of the amount of that material which is effective to alleviate psoriasis when applied alone and the amount of the material selected from Group II may satisfactorily vary from about 1/100th to about ⅓rd of the amount of that material which is effective to alleviate psoriasis when applied alone. When the combination also includes a permissibe dose of a glucocorticoid, the quantities of the selected material from Group I and from Group II may each be decreased, or one of them may be decreased to as much as one-half of its previously selected effective concentration. From the standpoint of the greatest combination or safety and effectiveness it is preferred that the combination include a glucocorticoid. In the presence of a permissive dose of a glucocorticoid in the composition, the quantities of the material selected from Group I may vary from about 1/100th to about ⅓rd of the amount of that selected compound which is effective to alleviate psoriasis when applied alone and the amount of the material selected from Group II may vary from about 1/100th to about ⅓rd of the amount effective to alleviate psoriasis when applied alone. In most instances, it is preferred to slightly exceed the minimum quantity determined to be effective and to produce the desired synergistic result in any given composition, for example, it is desirable to employ ¼th to ⅓rd more of each of the compounds from Group I and Group II which is established as the minimum effective composition for a given patient since such composition has wider general utility and exhibits satisfactory safety characteristics for a wide range of psoriasis patients.

I claim:

1. A process for treating proliferative skin diseases which comprises administering to the afflicted human or animal a composition containing as its active component at least one of the compounds selected from the groups:

1. A compound of the formula

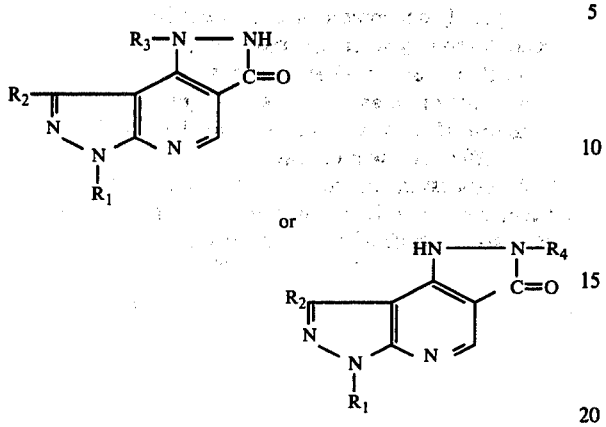

or wherein $R_1$ is selected from the group consisting of lower alkyl of 1 to 7 carbon atoms, cycloalkyl of 3 to 6 carbon atoms, phenyl, $(R_5)_n$-phenyl, $(R_5)_n$-phenyl-lower alkyl wherein $R_5$ is hydrogen, lower alkyl of 1 to 7 carbon atoms, halogen, and hydroxy-lower alkyl wherein the carbon chain is 1-3, n is 1 or 2, $R_2$ is selected from the group consisting of hydrogen and lower alkyl of 1 to 7 carbon atoms, $R_3$ is selected from the group consisting of hydrogen and lower alkyl of 1 to 7 carbon atoms, $R_4$ is phenyl and the physiologically acceptable acid addition salts thereof;

2. A compound of the formula

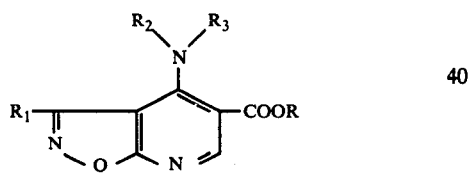

wherein R and $R_1$ are selected from the group consisting of hydrogen and lower alkyl of 1 to 3 carbon atoms, $R_2$ and $R_3$ are selected from the group consisting of hydrogen, lower alkyl of 1 to 4 carbon atoms, phenyl, benzyl, phenethyl and dialkylaminoalkyl in which alkyl is of 1 to 3 carbon atoms or taken together $R_2$ and $R_3$ form a heterocyclic ring selected from the group consisting of pyrrolidine, piperazino, piperidino, methylaziridino, 2,3-dimethylaziridino and 4-hydroxyethylpiperazino, and the pharmacologically acceptable acid addition salts;

3. A comound of the formula

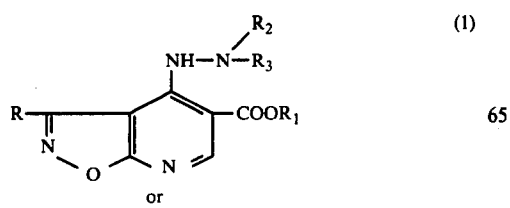

-continued

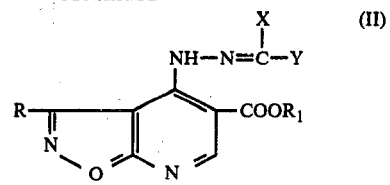

wherein R and $R_1$ each is hydrogen, lower alkyl of 1-8 carbon atoms, benzyl or phenethyl, $R_2$ is hydrogen, lower alkyl of 1-8 carbon atoms or phenyl, $R_3$ is hydrogen, lower alkyl of 1-8 carbon atoms or lower alkanoyl in which the acyl radical is of 1-8 carbon atoms, providing that only one R is a phenyl containing substituent, X represents hydrogen, lower alkyl, hydroxy-lower alkyl, phenyl or phenyl-lower alkyl, Y represents lower alkyl, phenyl, hydroxy-lower alkyl or phenyl-lower alkyl and together X and Y are cycloalkyl, and physiologically acceptable acid addition salts thereof;

4. A compound of the formula

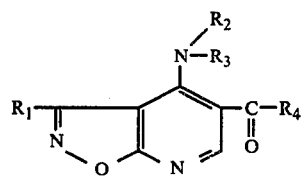

where $R_1$ is selected from the group consisting of hydrogen and lower alkyl of 1 to 3 carbon atoms, $R_2$ and $R_3$ are selected from the group consisting of hydrogen, lower alkyl of 1 to 4 carbon atoms, phenyl, benzyl, phenethyl and dialkylaminoalkyl in which alkyl is of 1-3 carbon atoms or taken together $R_2$ and $R_3$ from a heterocyclic ring, selected from the group consisting of pyrrolidino, piperazino, piperidino, methylaziridino, 2,3-dimethylaziridino and 4-hydroxyethylpiperazino, $R_4$ is selected from the group consisting of lower alkyl, cyclo-lower alkyl, phenyl, hydroxyphenyl and hydroxy-lower alkylphenyl, and the pharmacologically acceptable acid addition salts thereof;

5. A compound of the formula

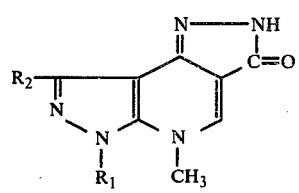

wherein $R_1$ is lower alkyl of 1 to 7 carbon atoms, phenyl, benzyl or phenethyl and $R_2$ is hydrogen or lower alkyl; or 6. A compound of the formula

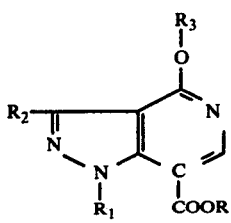

wherein R is hydrogen or alkyl of up to 12 carbon atoms, $R_1$ is hydrogen, lower alkyl of up to 12 carbon atoms, meta- or para-$R_4$, $R_5$-benzoyl, phenyl, benzyl or phenethyl, $R_2$ is hydrogen, lower alkyl of up to 12 carbon atoms, phenyl, benzyl or phenethyl, $R_3$ is lower alkyl of up to 12 carbon atoms, benzyl or phenethyl, $R_4$ and $R_5$ each is hydrogen, halogen, methyl or methoxy, and physiologically acceptable acid addition salts thereof;

said compounds being in association with a pharmaceutical carrier wherein said active component is present in an amount in the range of about 0.1 to about 15% w/v which is effective to alleviate a proliferative skin disease.

2. A process in accordance with claim 1 wherein said active component is administered in conjunction with a permissive dosage of a glucocorticoid.

* * * * *